United States Patent [19]

Mattler

[11] 4,026,294

[45] May 31, 1977

[54] COMBINATION CLAMPING/CUTTING APPARATUS AND METHODS OF USING SAME

[76] Inventor: Martin Mattler, 24575 Franklin Park Drive, Franklin, Mich. 48025

[22] Filed: Oct. 8, 1975

[21] Appl. No.: 620,812

[52] U.S. Cl. .............................. 128/305; 128/346
[51] Int. Cl.² ................... A61B 17/32; A61B 17/08
[58] Field of Search ............................ 128/305, 346

[56] References Cited

UNITED STATES PATENTS

| 1,918,700 | 7/1933 | Harris | 128/305 |
| 3,106,919 | 10/1963 | Churchville | 128/346 |
| 3,175,556 | 3/1965 | Wood et al. | 128/346 X |
| 3,323,208 | 6/1967 | Hurley, Jr. | 128/346 X |
| 3,566,873 | 3/1971 | Melges | 128/305 |
| 3,706,312 | 12/1972 | Melges | 128/346 X |

*Primary Examiner*—Channing L. Pace
*Attorney, Agent, or Firm*—Irving M. Weiner; Pamela S. Austin

[57] ABSTRACT

A device for clamping and then cutting an umbilical cord in separate and distinct clamping and cutting steps. Two parallel clamps are held together by two bridges held between the blades of a pair of scissors. As the blades move towards each other, the umbilical cord is first clamped, and then the scissors are removed from the bridges, and thereafter the scissors sever the umbilical cord. The bridges are then removed from the clamp affixed to the portion of the umbilical cord attached to the newborn child.

9 Claims, 6 Drawing Figures

U.S. Patent  May 31, 1977  4,026,294
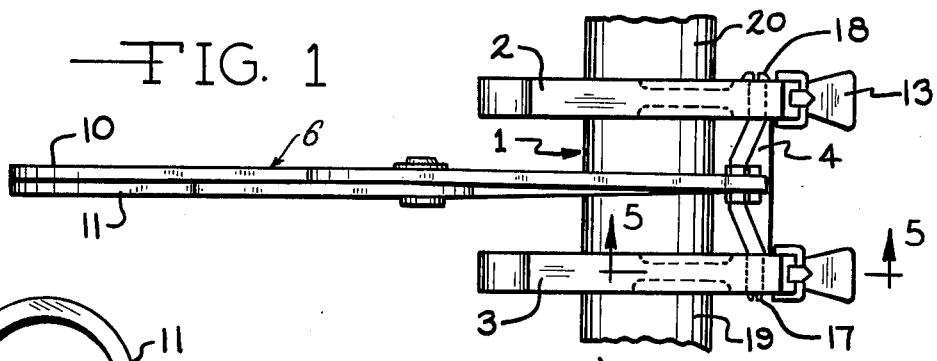
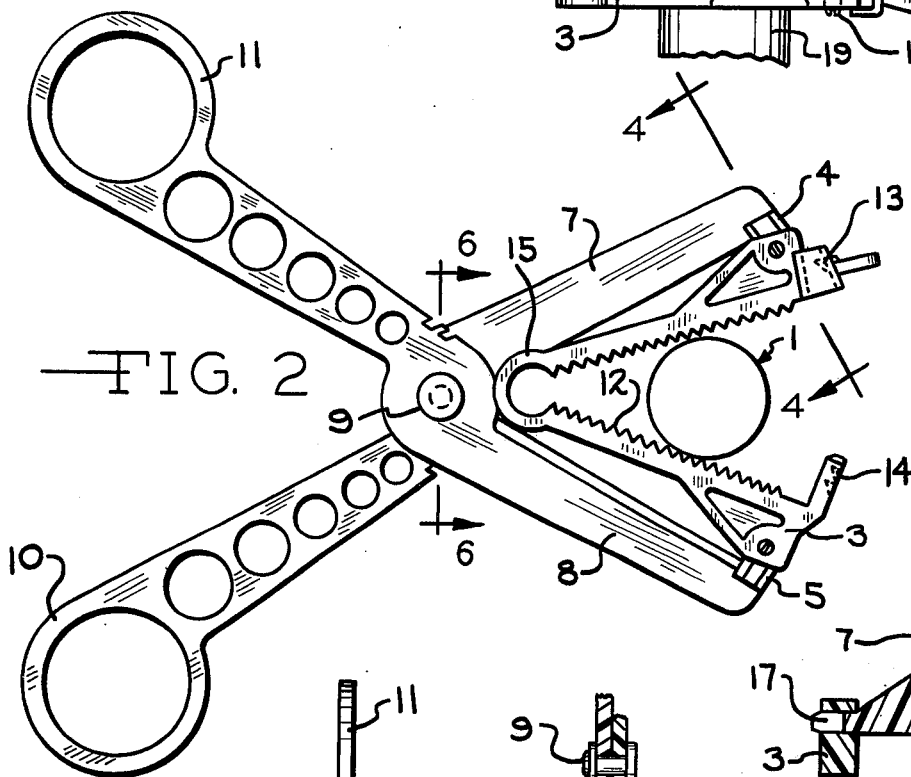
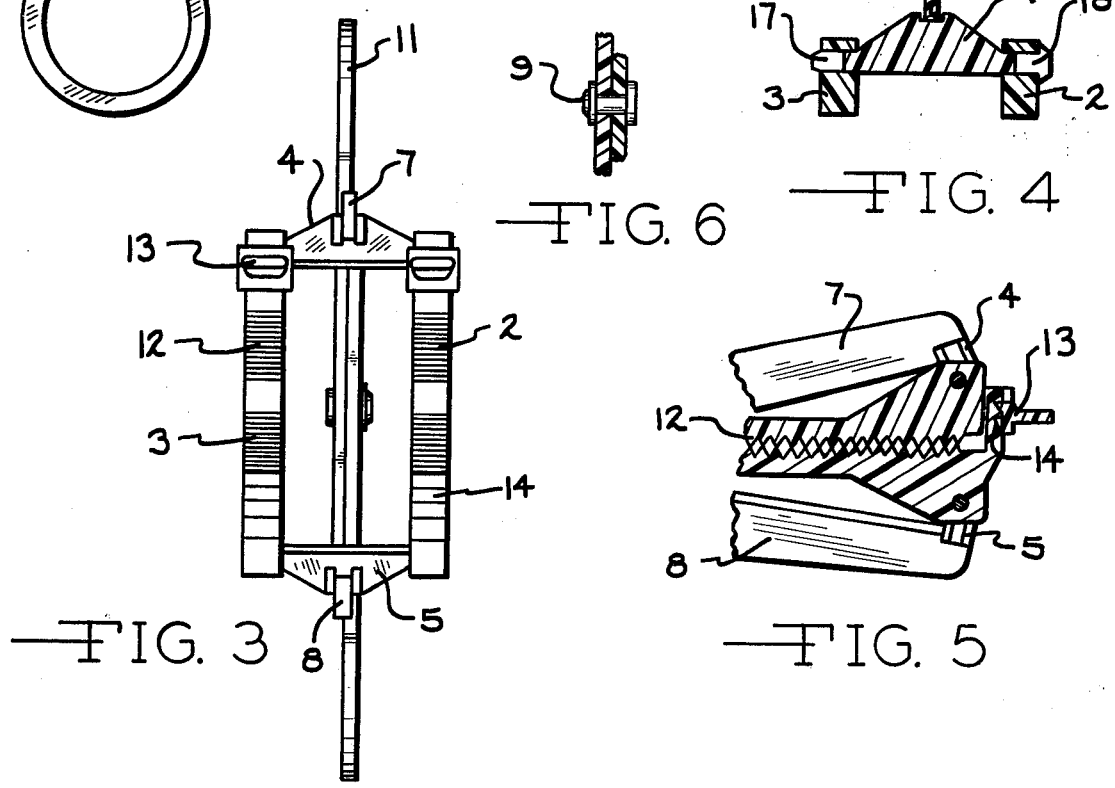

COMBINATION CLAMPING/CUTTING APPARATUS AND METHODS OF USING SAME

The present invention relates to an apparatus for clamping and severing an elongated member, and methods of constructing and utilizing such apparatus. In particular, the present invention relates to an apparatus for clamping and cutting flexible and/or deformable members, such as an umbilical cord, and to a novel method of utilizing such apparatus.

The phraseology "elongated member" as used herein is intended to connote an umbilical cord, an artery, a vein, a capillary, a conduit, a tube, a duct, and in general any flexible and/or deformable member which is capable of being clamped and then severed. Although the present invention will be referred to hereinafter in connection with the clamping and severing of an umbilical cord, the invention is not to be taken limited solely to use in connection with umbilical cords.

BACKGROUND OF THE INVENTION

The umbilical cord is a rope-like structure which connects the fetus (unborn child) to the placenta. The cord contains two arteries and one vein. The arteries carry blood containing waste products from the fetus to the placenta. The vein carries blood containing oxygen and food substances obtained from the mother's blood back to the fetus.

Heretofore, when a baby was born, the doctor had to very carefully and dexteriously cut the umbilical cord at a point close to the baby's abdomen. The scar, which remains throughout life, is call the umbilicus or naval.

Heretofore, various attempts have been made to provide a device which allegedly would clamp the umbilical cord and simultaneously cut the cord wherein the segments are separated and clamped. In this connection, reference is made to the prior art device disclosed in Churchville U.S. Pat. No. 3,106,919. However, such devices are difficult to mainpulate and have other attendant disadvantages. For example, such devices are difficult to manipulate and have a tendency to slip, especially when being handled by gloves or hands which are not completely free of fluids or moisture. The inability to grasp such devices in a non-slip manner is not alleviated or cured by providing the outer clamp surfaces with a non-slip formation.

The aforementioned slip condition is further accentuated by the lack of leverage provided by such prior art devices, which leverage is necessary to securely clamp and sever the umbilical cord.

Moreover, with the aforementioned prior art device it is necessary to first orient the device so that the clamp side with the blade remains on the mother's side of the cord for discarding with the placenta. A misorientation of such device, which is likely to occur because of the not easily viewable blade, may injuriously leave the clamp side with the blade on the child's side of the cord. This may result in infection and various other complications.

In addition, with the aforementioned prior art device, after the cord has been cut, it is then necessary to separate the pair of clamps by breaking the connecting bridge or spacer between the clamps. Ofttimes, the breaking of such bridge or spacer is not easily accomplished so that there is an unnecessary time delay in separating the newborn child from the placenta.

The aforementioned difficulties and disadvantages are avoided and eliminated by the present invention.

SUMMARY OF THE INVENTION

The present invention provides an apparatus for clamping and severing an elongated member, comprising, in combination, first means for clamping the elongated member, and second means for clamping the elongated member. The apparatus also includes third means operably and mechanically interconnected to the first and second means for maintaining the first and second means in a predetermined side-by-side relationship. The apparatus in a predetermined side-by-side relationship. The apparatus further includes fourth means operably and releasably interconnected to the third means for moving the first and second means to a closed position wherein the elongated member is clamped by the first and second means. The fourth means also severs the clamped elongated member.

The present invention also provides a novel method whereby the scissors' leverage is used to perform the clamping operation, and the clamping and cutting operations are separate and distinct operations.

It is an object of the present invention to provide a combination clamping and cutting apparatus for an umbilical cord whereby the leverage of the scissors is used for the clamping.

It is another object of the present invention to provide such an apparatus wherein the clamping step and the cutting step are separate and distinct operations.

Another object of the present invention is to provide an apparatus whereby the apparatus may be securely grasped and there is no necessity for directly handling the clamping members.

A further object of the present invention is to provide a combination clamping and cutting apparatus for an umbilical cord having releasable catches for releasing the clamps in a simple step.

Yet another object of the present invention is to provide a combination clamping and severing apparatus for an umbilical cord wherein the clamps and the cutting elements are separate and distinct elements.

A further object of the present invention is to provide a scissors-like component which initially holds the clamping members, and then is utilized to securely clamp such members on the umbilical cord, and then is removed from the bridge members, and is then used to sever the umbilical cord.

Other objects and advantages of the present invention will appear from the following description and appended claims reference being had to the accompanying drawings forming a part of this specification, wherein like reference characters are intended to designate corresponding parts in the several views.

BRIEF DESCRIPTION OF THE DRAWINGS

FIG. 1 illustrates a top plan view of an apparatus in accordance with a first embodiment of the present invention showing an umbilical cord disposed therein.

FIG. 2 depicts a side elevational view of the apparatus shown in FIG. 1.

FIG. 3 illustrates a side elevational view taken from the right side of FIG. 2, but with the umbilical cord removed for purposes of clarity.

FIG. 4 shows a sectional view taken along the line 4-4 in FIG. 2 to show the arrangement of the clamps, the bridge, and the scissors blade.

FIG. 5 depicts a sectional view taken along the line 5-5 shown in FIG. 1 showing the apparatus in its closed or clamped position, but prior to severance of the bridge.

FIG. 6 illustrates a sectional view taken along the line 6-13 6 of FIG. 2 to show the scissors pivot.

DETAILED DESCRIPTION OF A PREFERRED EMBODIMENT OF THE PRESENT INVENTION

Before explaining the present invention in detail, it is to be understood that the present invention is not to be limited in its applications or uses to the details of construction and arrangement of parts illustrated in the accompanying drawings, because the present invention is capable of other embodiments, variations and moficiations, and of being practiced or carried out in various ways. Furthermore, it is to be understood that the phraseology and terminology employed herein is for the purpose od description and illustration only, and is not for the purpose of limitation.

With reference to the drawings, there is shown an apparatus for clamping and severing an elongated member, such as an umbilical cord 1 as shown in FIGS. 1 and 2. The apparatus includes first means, such as a clamp 2, for clamping the cord 1, and second means, such as a clamp 3, for clamping the cord 1.

The apparatus also includes third means, such as bridges 4 and 5, operably and mechanically connected to clamps 2 and 3 for maintaining the clamps 2 and 3 in a predetermined side-by-side relationship.

The apparatus also includes fourth means, such as a pair of scissors 6, operably and releasably connected to the bridges 4 and 5 for moving the clamps 2 and 3 to a closed position wherein the cord 1 is clamped by the clamps 2 and 3. The pair of scissors 6 comprises scissors blade members 7 and 8 which are pivotally connected by a suitable pivoting device 9 (best shown in FIG. 6) and each being provided with finger grips 10 and 11, respectively.

With reference to FIGS. 2, 3 and 5, the clamps 2 and 3 are provided with staggered teeth 12 which mesh when closed. Each clamp 2 and 3 is also provided with a releasable catch 13 for mating with ratchet steps. The clamps 2 and 3 may be fabricated from plastic or any other suitable material.

Each clamp 2 and 3 is provided with a hinge portion 15 which normally biases the clamp 2 or 3 to be open in a free position. In accordance with a preferred embodiment of the present invention, when each clamp 2 or 3 is opened in a free position, the planes of the tips of the teeth 12 form a dihedral angle which is not less than 90°.

With reference to FIGS. 1-5, and in particular with reference to FIG. 4, each bridge 4 and 5 is provided with a seat 16 for accommodating an associated scissors blade 7 or 8, and two slotted ends 17 and 18. The ends 17 and 18 are slotted to facilitate assembly of the bridges 4 and 5 with the clamps 2 and 3 by way of compressing the slotted ends 17 and 18, inserting in associated apertures in the clamps 2 and 3, and then releasing the compression on the slotted ends 17 and 18 to leave the bridges assembled with the associated clamps. In accordance with a preferred embodiment of the present invention, the slotted end 17 may be molded to have a 10° angle between the sides forming the slot, but which angle is reduced substantially to zero when the end 17 is in its assembled or working position in the clamp 3. Again, in accordance with a preferred embodiment of the present invention, the slotted end 17 of the bridge is assembled with the clamp 3 for easy and subsequent removal therefrom where clamp 3 is to be employed on that portion of the umbilical cord remaining with the newborn child. In contrast, on the other end of the bridges 4 and 5 the slotted end 18 is provided with a flange for preventing removal of the slotted end 18 from the clamp 2 which, in accordance with a preferred embodiment of the present invention, will remain with that portion of the umbilical cord 1 associated with the mother's afterbirth, as explained in greater detail hereinbelow.

The operation or use of the invention will now be described. First, the clamps 2 and 3 and the bridges 4 and 5 are assembled as depicted in FIGS. 3 and 4. Then, the assembled clamps and bridges are placed in the pair of scissors 6 with the blades 7 and 8 releasably interconnected with or seated within the seat 16 of the bridges 4 and 5.

Then the assembled apparatus is positioned, as indicated in FIGS. 1 and 2, so that the cord 1 is between the teeth 12, and whereby the slotted end 17 of the bridges 4 and 5 is disposed toward the newborn infant side of the cord 1. To facilitate this orientation, an optional feature of the present invention contemplates power keying the clamp 3 to assure that the clamp carrying the slotted end 17 is disposed toward the newborn infant. In FIG. 1 the umbilical cord 1 has been sub-designated 19 to represent the portion of the umbilical cord adjacent the newborn infant, and 20 to designate the portion of the umbilical cord adjacent the mother or afterbirth.

Using the leverage of the scissors 6, the blades 7 and 8 urge the bridges 4 and 5 towards each other so that the clamps 2 and 3 close into a clamped position, as represented in FIG. 5. In this clamped position, it should be noted that the releasable catch 13 has mated with a ratchet step 14 to prevent inadvertent opening of the clamps. In this same position, although not illustrated in FIG. 5, the cord 1 is firmly and securely clamped between the teeth 12 of the clamps 2 and 3, but the teeth 12 being so shaped as not to break or cut the clamped cord 1.

After the cord 1 has been clamped, the scissors 6 are opened to remove the blades 7 and 8 from the bridge seats 16. Then, the scissors 6 are moved toward the left as viewed in FIGS. 1, 2 and 5 to bring the blades 7 and 8 clear of the bridges 4 and 5. The scissors 6 are then closed again to neatly sever the cord 1 into the cord portions 19 and 20. The scissors are then opened and then removed from the hand of the operator. It should be carefully noted that up to this point it was not necessary to directly handle the clamps and bridges, and that the scissors were held by the operator during the separate and distinct step of positioning the clamps about the cord 1, the separate and distinct step of clamping the cord 1, the separate and distinct step of opening the scissors to unseat the blades from the bridges, and the separate and distinct step of closing the scissors to sever the cord 1.

Thereafter, the slotted ends 17 of the bridges 4 and 5 may be readily removed from the clamp 3 to leave the bridges 4 and 5 on the clamp 2 with the cord portion 20 remaining with the afterbirth. The clamp 3 remains on cord portion 19 with the baby until the cord is dry in accordance with accepted medical procedures, which is normally 24 to 36 hours.

It should be noted that the clamps may be readily removed from the clamping position by movement of the easily-accessible releasable catch 13 for displacement from the ratchet step 14. No tools or use of fingernails in internal portions of the clamps is necessary to unclamp the same.

If desired, the bridges 4 and 5 may be removed from the clamp 3 before the cutting step.

In accordance with a preferred embodiment of the present invention, the bridges 4 and 5 may be fabricted from nylon, or from some other suitable plastic material.

It should also be carefully noted, that one of the primary advantages over the prior art developments resides in the fact that there is no danger of leaving an unsanitary cutting member with any portion of the umbilical cord.

It will be evident from the description set forth hereinabove that there is herein provided a novel apparatus and method which satisfies all of the objects of the present invention, as well as others, including many advantages of great practical utility and commercial importance. It should also be noted that the portions of the apparatus maybe sterilized and re-used if desired.

Furthermore, because many embodiments of the present invention may be made of this inventive concept, and because many modifications and variations may be made of the particular embodiment hereinbefore shown and described, it is to be understood that all matter herein is to be interpreted merely as illustrative, and not in a limiting sense.

Another important feature of the releasable catch/ratchet step 13, 14 arrangement is to permit further adjustment for re-positioning the clamp 3 relative to the cord portion 19, or for adjustments to accommodate changes in the size of the cord, e.g., which may change in diameter due to drying out, etc.

I claim:

1. An apparatus for clamping and severing an elongated member, comprising, in combination:
   first means for clamping said elongated member;
   second means for clamping said elongated member;
   third means operably and mechanically interconnected to said first and second means for maintaining said first and second means in a predetermined side-by-side relationship; and
   fourth means operably and releasably interconnected to said third means for moving said first and second means to a closed position wherein said elongated member is clamped by said first and second means;
   said fourth means adapted to be removed from said third means; and
   said fourth means when so removed adapted to sever said clamped elongated member.

2. An apparatus characterized substantially in accordance with claim 1, wherein said fourth means comprises a pair of scissors.

3. An apparatus characterized substantially in accordance with claim 1, wherein:
   said third means includes a seat in the form of a groove; and
   said fourth means includes at least one blade member which is releasably disposed within said groove.

4. An apparatus characterized substantially in accordance with claim 1, wherein:
   said first means includes at least one first aperture therethrough;
   said second means includes at least one second aperture therethrough; and
   said third means includes a first slotted end portion for fitting within said first aperture of said first means, and a second slotted end portion for fitting within said second aperture of said second means.

5. An apparatus characterized substantially in accordance with claim 1, wherein:
   said first and second means are both provided with ratchet steps at one end thereof, and a releasable catch for mating with said ratchet steps; and
   said releasable catch being molded unitary with its associated first and second means and having an external tab portion for permitting pivoting said releasable catch.

6. An apparatus characterized substantially in accordance with claim 2, wherein:
   said third means includes a first bridge member which is releasably interconnected with a first end of said second and third means, and a second bridge member which is releasably interconnected with said first and second means at an end opposite to that of said first end.

7. An apparatus characterized substantially in accordance with claim 6, wherein:
   each said bridge member is provided with a first slotted end portion, and a second slotted end portion which is disposed opposite to said first slotted end portion;
   and only one of said slotted end portions being provided with a flanged abutment.

8. An apparatus characterized substantially in accordance with claim 1, wherein:
   said fourth means is provided with a pair of blade members for severing said clamped elongated member; and
   said blade members are disposed between said first and second means for clamping said elongated member.

9. An apparatus characterized substantially in accordance with claim 8, wherein:
   said third means includes a first bridge member which is releasably interconnected with a first end of said second and third means, and a second bridge member which is releasably interconnected with said first and second means at an end opposite to that of said first end.

* * * * *